(12) United States Patent
Barbut

(10) Patent No.: US 6,533,800 B1
(45) Date of Patent: Mar. 18, 2003

(54) DEVICES AND METHODS FOR PREVENTING DISTAL EMBOLIZATION USING FLOW REVERSAL IN ARTERIES HAVING COLLATERAL BLOOD FLOW

(75) Inventor: Denise R. Barbut, New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 0 days.

(21) Appl. No.: 09/915,648

(22) Filed: Jul. 25, 2001

(51) Int. Cl.[7] ............ A61M 29/00; A61B 17/22
(52) U.S. Cl. ............ 606/194; 606/200; 606/159
(58) Field of Search ............ 604/96.01, 167.01, 604/264; 606/194, 200, 159; 623/3.13

(56) References Cited

U.S. PATENT DOCUMENTS

| | | | |
|---|---|---|---|
| 4,883,459 A | * 11/1989 | Calderon | 604/101.01 |
| 4,921,478 A | 5/1990 | Solano et al. | |
| 5,423,742 A | 6/1995 | Theron | |
| 5,431,639 A | * 7/1995 | Shaw | 604/264 |
| 5,462,529 A | * 10/1995 | Simpson et al. | 604/101.04 |
| 5,599,307 A | 2/1997 | Bacher et al. | |
| 5,765,568 A | 6/1998 | Sweezer, Jr. et al. | |
| 5,769,812 A | 6/1998 | Stevens et al. | |
| 5,833,645 A | 11/1998 | Lieber et al. | |
| 5,833,650 A | * 11/1998 | Imran | 604/508 |
| 5,938,645 A | 8/1999 | Gordon | |
| 5,941,896 A | * 8/1999 | Kerr | 606/192 |
| 6,099,497 A | * 8/2000 | Adams et al. | 604/101.01 |
| 6,146,370 A | 11/2000 | Barbut | |
| 6,156,005 A | * 12/2000 | Theron | 604/101.05 |
| 6,168,579 B1 | * 1/2001 | Tsugita | 606/200 |
| 6,206,868 B1 | 3/2001 | Parodi | |
| 6,413,235 B1 | * 7/2002 | Parodi | 606/200 |
| 6,454,741 B1 | * 9/2002 | Muni et al. | 604/509 |

OTHER PUBLICATIONS

Theron et al., "New Triple Coaxial Catheter System for Carotid Angioplasty with Cerebral Protection," *American Journal of Neuroradiology*, Sep./Oct. 1990, pp. 869–874, vol. 11, American Society of Neuroradiology, USA.

Jochem et al., "Radiographic Anatomy of the Coronary Collateral Circulation," *Anatomy of Coronary Collaterals*, Sep. 1972, pp. 50–60.

* cited by examiner

*Primary Examiner*—Michael J. Milano
*Assistant Examiner*—Sarah Webb
(74) *Attorney, Agent, or Firm*—O'Melveny & Myers LLP

(57) ABSTRACT

The invention provides a medical device having a catheter and one or more expandable constricting/occluding members. The catheter is adapted for use with therapeutic or diagnostic devices, including an angioplasty/stent catheter and an atherectomy catheter. The constrictor/occluder is mounted at the distal end of the catheter. Manometers may be mounted distal to one or more constrictors for measuring pressure distal to the constrictor(s). Methods of using the devices are disclosed for preventing distal embolization during extracranial or intracranial carotid artery, vertebral artery, or coronary artery procedures, or procedures involving any vessel having collateral flow by reversing flow in the diseased vessel.

15 Claims, 9 Drawing Sheets ized devices capable of reversing blood flow in a first artery so that blood flows into a second artery during an invasive procedure, thereby avoiding distal embolization of vascular debris in the first artery.

DEVICES AND METHODS FOR PREVENTING DISTAL EMBOLIZATION USING FLOW REVERSAL IN ARTERIES HAVING COLLATERAL BLOOD FLOW

FIELD OF THE INVENTION

The present invention relates generally to devices and methods useful in treating patients with occlusive vascular disease. More specifically, the invention provides devices capable of reversing blood flow in a first artery so that blood flows into a second artery during an invasive procedure, thereby avoiding distal embolization of vascular debris in the first artery.

BACKGROUND OF THE INVENTION

Collateral channels are present in arterial, venous, and lymphatic circulation throughout the body. Collateral circulation is established through connection(s) or anastomoses between two vessels supplying or draining two adjacent vascular regions. Blood supply to an organ is maintained through these collateral channels when the main vessel is obstructed. Collateral circulation, therefore, provides a compensatory mechanism that allows amelioration of the detrimental effect of blood flow cessation due to obstruction of a vascular pathway.

The areas of the body where collateral blood flow is of particular importance are that of the cerebral and coronary circulation where interruption or cessation of blood supply to the brain or the heart may be have devastating consequences, e.g., causing stroke or myocardial infarction. Collateral circulation is also present in the extremities. Occlusion of blood supply to the extremities is usually due to atherosclerosis. Clinical symptoms depend upon the extent of obstruction, the rate of progression, the vessels involved, and whether collateral flow exists.

Current treatment of vascular occlusive disease includes percutaneous transluminal angioplasty (PTCA), thromboendarterectomy, bypass graft using woven prosthetic tube or autogenous vein anastomosed end-to-side to the vessel above and below the obstruction, or resection with graft replacement. Unfortunately, one common complication is distal embolization of vascular debris, e.g., calcium, atheromatous plague, thrombi, fat, and vascular tissue, generated during the procedures. Distal embolization of debris to a coronary artery can cause further myocardial ischemia and infarction. Embolization of debris to the distal extremities may cause gangrene of the toes and foot.

New devices and methods are thus needed for patients undergoing vascular procedures for treatment of occlusive vascular disease, devices that minimize the risk of distal embolization and end organ damage.

SUMMARY OF THE INVENTION

The invention provides devices and methods for preventing organ ischemia and infarction in patients undergoing vascular procedures, including angioplasty, stent placement, and/or filter insertion, by reversing blood flow from a first artery, vein, or lymphatic duct, into a second artery by use of collateral circulation. In this way, embolic debris generated as a result of placing instrumentation within a diseased first vessel is diverted to the second vessel, thereby minimizing embolization to the distal vessels supplied by the diseased vessel. It will be understood that the devices and methods disclosed herein are useful in any region of the body where flow reversal is possible.

The invention utilizes devices comprising a catheter having one or two expandable constricting members at a distal region. Each constrictor may be a balloon, in certain cases a toroidal balloon, or a device of any other appropriate shape, so that it can fully or partially obstruct blood flow. The lumen of the catheter may be adapted for insertion of a therapeutic instrument, such as an angioplasty, atherectomy, and/or stent catheter. A manometer is optionally mounted proximal and/or distal to the constricting member for monitoring blood pressure proximal and/or distal the constrictor.

The terms obstruction, occlusion, and constriction are used interchangeably herein to refer to partial or complete blockage of a vessel, and to any of the devices that provide such blockage. The devices comprise an obstructing, occluding, or constricting mechanism, in certain cases a balloon, distally mounted on a catheter for delivery to a vessel, such as the left main coronary artery. The obstructor, occluder, and/or constrictor is collapsed to facilitate insertion into and removal from the vessel, and expanded during use to at least partially obstruct blood flow.

The occluder-constrictor is mounted near the distal end of the catheter, in certain cases proximal to a port. Each balloon occluder and constrictor communicates with an inflation lumen and an inflation port at the proximal end of the catheter. In certain embodiments, the catheter will include first and second constriction/occlusion members. The second constrictor may be mounted on a second member that is slideably insertable through the catheter, and passes beyond the first constrictor. In this way, the second member and the second constrictor are moveable longitudinally relative to the first constrictor. In other embodiments, the constrictor may comprise a balloon having one or more than one opening at its center for the passage of blood, or may consist of more than one expandable balloons allowing passage of blood through the gap or gaps between the arterial wall and the expanded balloons. The proximal end of the catheter may include a hemostatic valve.

In still another embodiment, the catheter includes a second lumen communicating with a proximal end and an infusion port at its distal end. The port is located distal to the distal port of the catheter. The second lumen and its port are adapted for delivering a pharmaceutical agent to the carotid, coronary, iliac, brachiocephalic and/or subclavian arteries, including an angiographic dye. Any devices and methods described in Barbut, U.S. Pat. No. 6,146,370, and in U.S. application Ser. No. 09/792,732, filed Feb. 23, 2001; Ser. No. 09/792,600, filed Feb. 23, 2001; and Ser. No. 09/847,425, filed May 1, 2001, all incorporated herein by reference in their entirety, may also be used in the procedures described herein.

The catheters may be used anywhere in the body for flow reversal in an artery, vein, or lymphatic duct having a proximal segment that branches into first and second distal segments. The vessels are selected so that the first distal segment has a source of collateral blood or lymphatic flow and typically will also have a lesion. The distal end of the catheter is inserted into the proximal segment. The expandable device is located within the proximal segment. The expandable constricting-occluding device is expanded to at least partially obstruct the proximal segment. This causes flow to reverse in the first distal segment and to pass over the lesion and toward the second distal segment.

In one application, the invention provides methods for reversing flow from a coronary artery having an atheromatous lesion into another coronary artery. For example, the methods are useful in reversing flow from an occluded left anterior descending (LAD) artery and into the left circumflex (LCx) artery. Using the devices described above, the distal end of the catheter is inserted into the left main coronary artery which branches into the LAD and LCx arteries. The catheter can be inserted over a guidewire through an incision on a peripheral artery, including the femoral artery, the subclavian artery, or the brachial artery. The catheter is positioned to locate the constricting member within the left main coronary artery. The constrictor is expanded to completely or partially occlude the left main coronary artery. At a critically low pressure distal to the constriction, blood flow in the LAD artery is reversed to pass over the atheromatous lesion and into the LCx artery. This reversal occurs because the LAD receives collateral blood flow from other coronary arteries downstream of the occlusion. The flow reversal can be verified fluoroscopically with dye. If flow reversal fails to occur or if augmentation of flow reversal is desired, a second constricting member is expanded in the LCx artery, further reducing the LCx distal pressure and enhancing reversal of flow to the LCx. A blood filter may be inserted through the catheter and deployed in the LCx artery to prevent distal embolization in that artery. After blood reversal is confirmed, procedures on the LAD artery may be performed by advancing a therapeutic or diagnostic instrument through the lumen and port of the catheter distal to the constrictor. An angioplasty catheter, for example, can be introduced to reduce the obstructing atheroma in the LAD artery without fear of distal embolization.

In another example, the distal end of the catheter is inserted into the right common iliac artery to treat an occluding lesion in the right internal iliac artery. The catheter is positioned to locate the constricting member in the right common iliac artery. The constrictor is expanded to completely or partially occlude the common iliac artery. At a critically low pressure, blood flow in the right internal iliac artery is reversed into the right external iliac artery. This reversal occurs because the right internal iliac artery receives collateral blood flow from the left internal iliac artery and pelvic vessel. The same procedure could be done on the left common iliac artery. The flow reversal can be verified fluoroscopically with dye.

The invention also provides methods for reversing flow in a carotid artery which branches into first and second distal segments, where the first distal segment has an atheromatous lesion. More specifically, the methods are useful in reversing flow down an internal carotid artery (ICA) and up the external carotid artery (ECA), where both the ICA and the ECA are distal segments of the common carotid artery (CCA). In another method using the devices described above, the distal end of the catheter is inserted into the CCA. The catheter can be inserted over a guide wire through an incision on a peripheral artery, including the femoral artery, the subclavian artery, the brachiocephalic artery, or the common carotid artery. The catheter is positioned to locate the occluder within the CCA, and then to locate the constrictor (when present) within the ECA by operating the second member and the constrictor through the catheter. The occluder is expanded to completely or partially occlude the CCA. At a critically low CCA pressure, blood flow in the ICA is reversed to pass over the atheromatous lesion and into the ECA. The flow reversal can be verified fluoroscopically with dye. If flow reversal fails to occur or if augmentation of flow reversal is desired, the ECA constrictor is expanded, further reducing the pressure in the ECA to facilitate reversal of flow down the ICA and into the ECA. After blood reversal is confirmed, procedures on either the ICA or bifurcation of the CCA can be performed by advancing a therapeutic or diagnostic instrument through the lumen and port of the catheter distal to the occluder. An atherectomy catheter, for example, can be introduced to remove the atheroma in the ICA without fear of distal embolization.

In another method using the devices described above, a technique for treating a vertebral artery stenosis or dissection without risk of distal embolization is provided. A distal end of the catheter is inserted into the left or right subclavian artery in a retrograde or antegrade direction through an incision made on a peripheral artery, such as the brachial, the femoral artery, the subclavian artery, or the brachiocephalic artery. A constricting member carried at the distal end of the catheter is located in the unilateral subclavian artery upstream the vertebral artery in which flow reversal is desired. The constricting member is expanded to constrict or occlude the subclavian or innominate artery. This results in progressive reduction of blood pressure downstream of the constrictor, which ultimately results at a critical pressure level in reversal of blood flow from the higher-pressure vertebral artery to the lower-pressure innominate, subclavian, and/or brachiocephalic artery. The flow reversal can be verified fluoroscopically with dye. In certain methods, the lesion within the vertebral artery is then treated by advancing a therapeutic instrument into the unilateral vertebral artery to reduce the stenosis. The embolic debris generated during the procedure will flow toward the innominate, subclavian, and/or brachiocephalic artery and arteries of the extremity, or into a filter deployed in one of these arteries, thereby preventing stroke from distal vertebral embolization.

In another method of using the devices described above, the distal end of the catheter is inserted into the right brachiocephalic artery. The catheter can be inserted over a guidewire through an incision on a peripheral artery, including the femoral artery, the subclavian artery, or the brachiocephalic artery. The catheter is positioned to locate the constricting member within the right brachiocephalic artery. The constrictor is expanded to completely or partially occlude the right brachiocephalic artery. At a critically low brachiocephalic pressure distal the constriction, blood flow in the carotid and vertebral arteries is reversed to pass over the atheromatous lesion and into the right subclavian artery. The flow reversal can be verified fluoroscopically with dye. If flow reversal fails to occur or if augmentation of flow reversal is desired, a second constricting member is expanded in the right subclavian artery, further reducing the pressure in the subclavian artery to facilitate reversal of flow down the carotid artery and into the subclavian artery.

It will be understood that there are several advantages in using the devices and methods disclosed herein for reversing blood flow in arteries having collateral circulation. For example, the devices and methods (1) prevent distal embolization of an artery, such as the coronary arteries, during interventional procedures, (2) can be used to introduce a variety of diagnostic or therapeutic instruments into the vessel, (3) can be used in any procedures which require instrumentation within an artery, (4) can be used in the angiogram or fluoroscopy suite available in most hospitals, (5) require only one incision site for entry, and (6) can be used to perform an interventional procedure with distal protection (e.g., a distal filter) in a healthy artery, and without crossing the lesion.

DETAILED DESCRIPTION

Figure 1A:
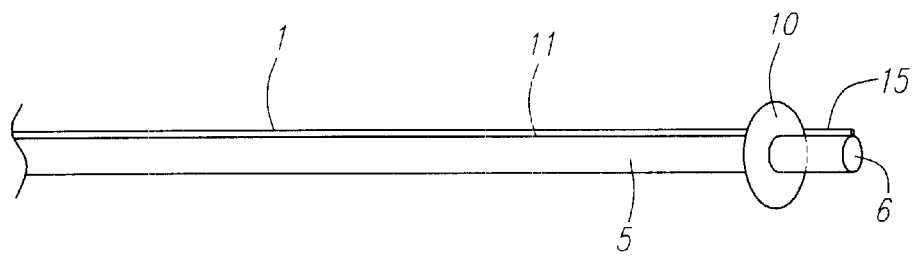
FIG. 1A depicts a distal region of a medical device having an occluding member for prevention of acute stroke during use of instrumentation in a vessel.

Balloon catheters useful for achieving flow reversal in arteries having collateral circulation were described in Barbut, U.S. Pat. No. 6,146,370, and U.S. application Ser. No. 09/792,732, filed Feb. 23, 2001; Ser. No. 09/792,600, filed Feb. 23, 2001; and Ser. No. 09/847,425, filed May 1, 2001, incorporated herein by reference in their entirety. FIG. 1A depicts one embodiment of the device for preventing distal embolization during use of vascular instrumentation. The device comprises catheter 1 and balloon occluder 10. The catheter has lumen 5 communicating with a proximal end and port 6 at a distal end. The lumen and port are adapted for introduction of therapeutic or diagnostic instruments, e.g., an atherectomy catheter, angioplasty catheter, and stent, to a carotid artery. Balloon occluder 10, communicating with inflation lumen 11, is mounted on the distal end of the catheter proximal to port 6. Manometer 15 is mounted distal to occluder 10 for monitoring blood pressure downstream the occluder.

Figure 1B:
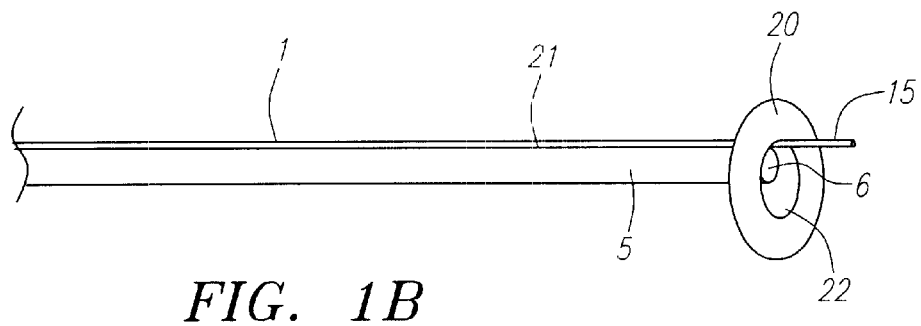
FIG. 1B depicts a distal region of another medical device having a constricting member.

FIG. 1B depicts another embodiment of the device having constricting member 20 mounted on a distal region of the catheter proximal to port 6. Constricting member 20 communicates with inflation lumen 21. The constrictor has central opening 22 that allows passage of blood. Manometer 15 is mounted distal to constrictor 20 for monitoring blood pressure downstream the constrictor.

Figure 2A:
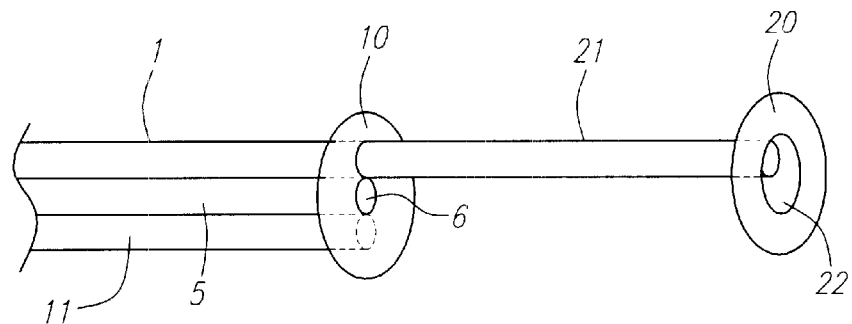
FIG. 2A depicts a distal region of another medical device having a constricting member distal an occluding member.

FIG. 2A depicts another embodiment of the device comprising catheter 1, balloon occluder 10, and constrictor 20. Lumen 5 of the catheter communicates with port 6 at distal end 7. The lumen and port are adapted for introduction of therapeutic or diagnostic instruments. Balloon occluder 10, communicating with inflation lumen 11, is mounted on the distal end of the catheter proximal to port 6. Balloon constrictor 20, communicating with inflation lumen 21, is mounted distal to port 6 and first occluder 10. The constrictor has central opening 22 that allows passage of blood. Inflation lumen 21 is an elongate member which, in certain embodiments, is slidably inserted through catheter 1, and is moveable longitudinally relative to catheter 1 and occluder 10.

Figure 2B:
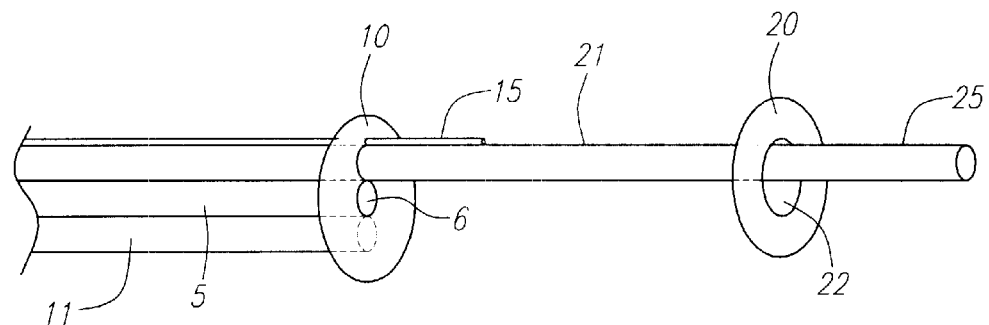
FIG. 2B depicts a distal region of another obstruction device having a manometer.

FIG. 2B depicts another embodiment of the device having two manometers. Manometer 15 is mounted distal to occluder 10 for measuring blood pressure between the occluder and the constrictor. Manometer 25 is mounted distal to constrictor 20 for measuring blood pressure downstream from constrictor 20. Any of the manometers of any device described herein will be understood to include a tube communicating with a pressure gauge at the proximal end of the catheter.

Figure 3:
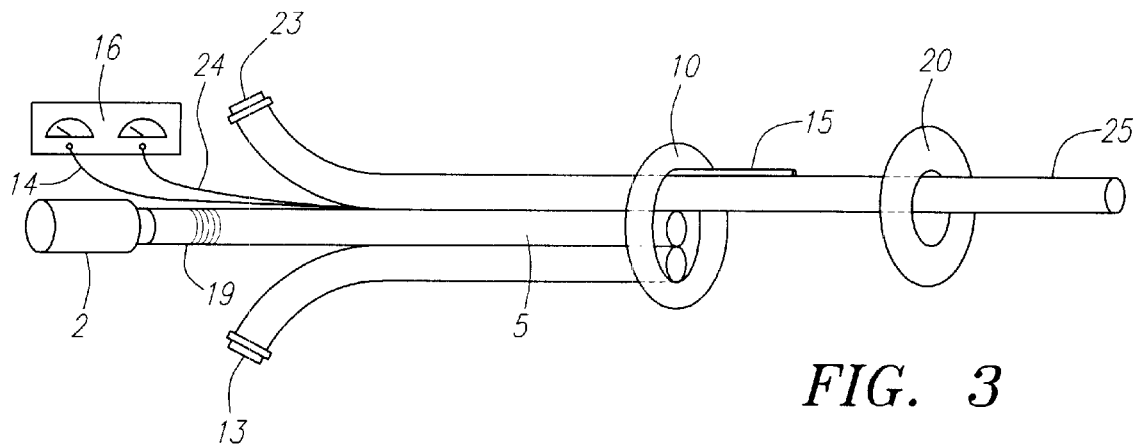
FIG. 3 depicts an obstruction device having a hemostatic valve and pressure monitor at its proximal end.

In FIG. 3, proximal ends 14 and 24 of respective manometers 15 and 25 are connected to pressure monitor 16 for measuring blood pressure proximal and distal the constrictor. Inflation ports 13 and 23 communicate, respectively, with inflation lumens 11 and 21 for expanding balloon occluder 10 and constrictor 20. Lumen 5 of the catheter communicates with proximal end 2, which includes hemostatic valve 19.

Figure 3A:
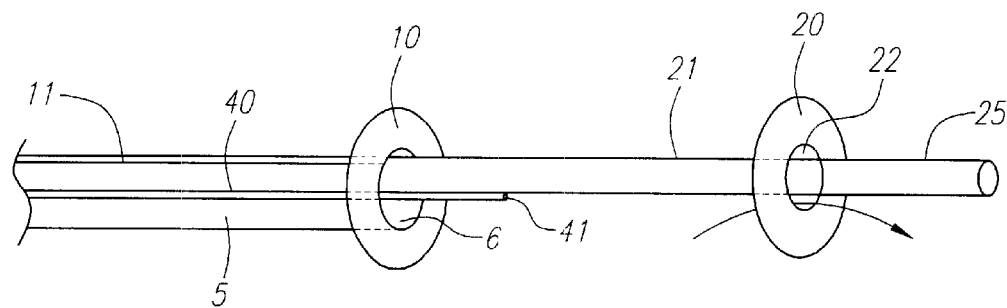
FIG. 3A depicts another embodiment of the device having a proximal occluder and a distal constrictor.
Figure 3B:
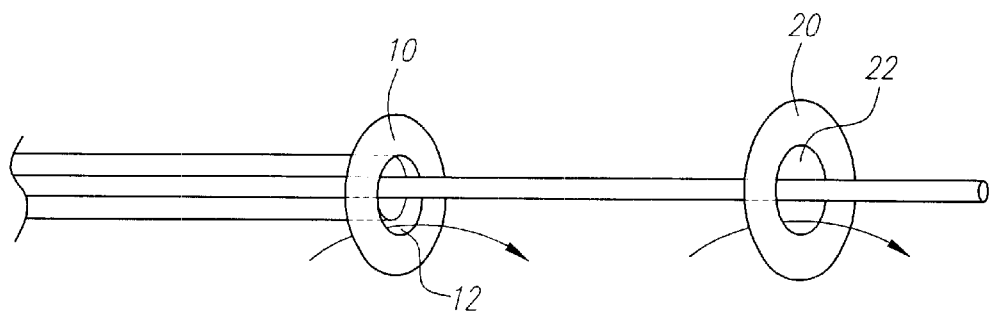
FIG. 3B depicts another embodiment of the device having a proximal constrictor and a distal constrictor.
Figure 3C:
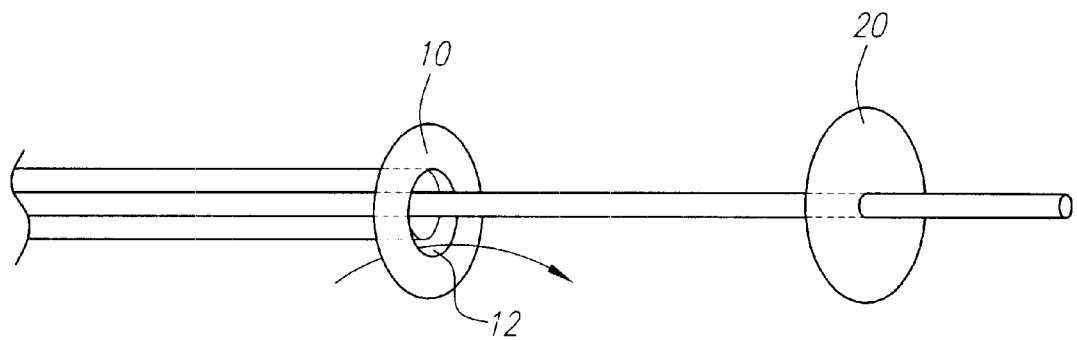
FIG. 3C depicts another embodiment of the device having a proximal constrictor and a distal occluder.
Figure 3D:
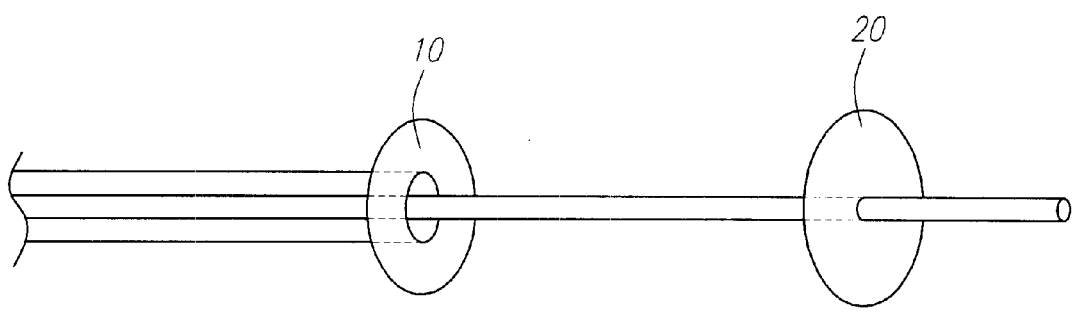
FIG. 3D depicts another embodiment of the device having a proximal occluder and a distal occluder.

FIGS. 3A, 3B, 3C, and 3D depict alternative devices for use in the methods described herein. Each catheter has first balloon 10 and second balloon 20. All combinations of constrictors and occluders are contemplated. Thus, first balloon 10 may be an occluder, and second balloon 20 may be a constrictor (FIG. 3A). Alternatively, first balloon 10 may be a constrictor, and second balloon 20 may be a constrictor (FIG. 3B). Alternatively, first balloon 10 may be a constrictor, and second balloon 20 may be an occluder (FIG. 3C). Alternatively, first balloon 10 may be an occluder, and second balloon 20 may be an occluder (FIG. 3D).

Figure 4A:
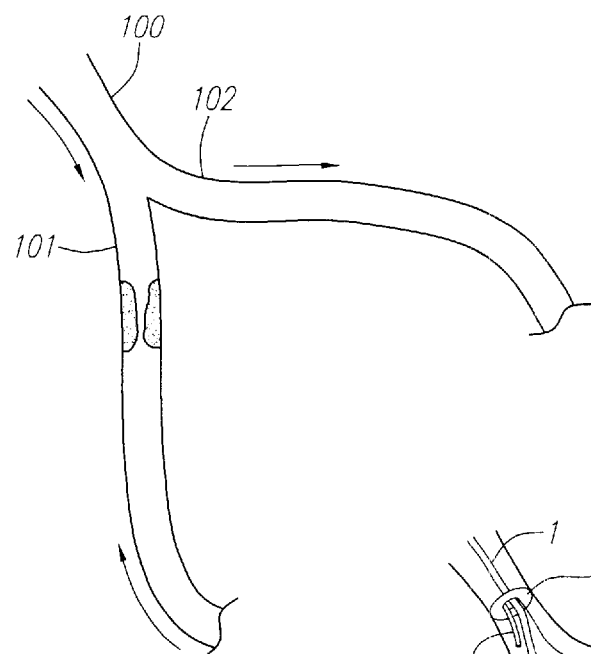
FIG. 4A depicts an occluding lesion in the proximal left anterior descending artery.

FIG. 4A depicts an atheromatous lesion located in a proximal segment of left anterior descending artery 101. Blood flows normally from left main coronary artery 100 which bifurcates into LAD artery 101 and left circumflex artery 102. The ischemic myocardium supplied by the distal LAD artery generally receives some blood flow from the LCx artery and the right coronary artery since the LAD artery is well collateralized.

Figure 4B:
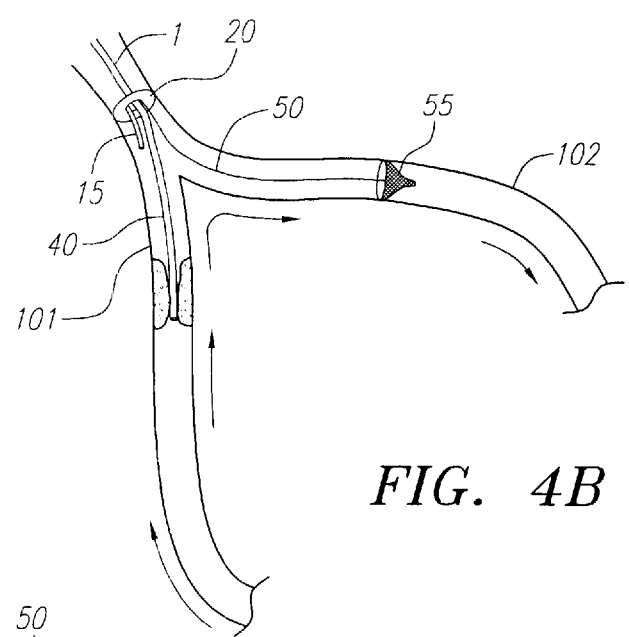
FIG. 4B depicts an expanded constrictor of FIG. 1B causing reversal of blood flow from the left anterior descending artery to the left circumflex artery during angioplasty.

In using the device of FIG. 1B to treat the atheromatous lesion in the LAD artery of FIG. 4A, a percutaneous incision is first made on a peripheral artery, such as the femoral artery. A guidewire is inserted through the incision into the ascending aorta in a retrograde direction. Alternatively, the guidewire is inserted into the right brachiocephalic artery from an incision in the left subclavian artery or left brachial artery in a retrograde direction, or in a retrograde direction through the right subclavian artery. The distal end of the catheter is inserted over the guidewire, so that constrictor 20 is positioned in the left main coronary artery 100 as shown in FIG. 4B; where needed, a guiding catheter can also be used. The guidewire is then removed from the catheter.

Constrictor 20 is slowly expanded to constrict left main coronary artery 100, causing progressive decline in the proximal LAD and LCx arterial pressure and greater pressure differential across the atheromatous lesion. The pressure in the LAD distal to the constrictor can be measured by manometer 15. At a critically low pressure in the proximal LAD artery, blood flow in LAD artery 101 reverses to pass over the atheromatous lesion and into LCx artery 102. The reversal of blood flow in the LAD and into the LCx artery can be verified fluoroscopically with dye. After reversal of blood flow is established, a therapeutic instrument, such as angioplasty catheter 40, can be inserted through the lumen of device 1 to treat the atheromatous lesion. Embolic materials, such as calcium, thrombi, atheromatous plaque, or tissue debris, are diverted into the LCx artery, thereby preventing or minimizing distal embolization down the LAD artery. To prevent distal embolization of vascular debris in the LCx artery, optional filter 55 mounted on guidewire 50 or a catheter may be inserted through the lumen of device 1 and deployed in the LCx artery as shown in FIG. 4B. Having the filter deployed in the healthy LCx artery to trap embolic debris is more desirable than having the filter deployed distal the atheromatous lesion because crossing of the lesion may cause unwanted complication, such as embolization caused by inadvertent plaque rupture.

Figure 4C:
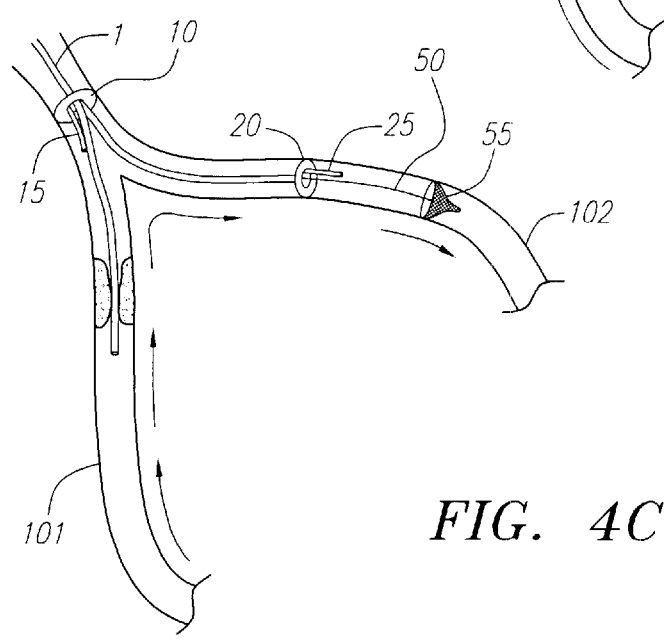
FIG. 4C depicts the use of the device of FIG. 3B to treat the occluding lesion of FIG. 4A using flow reversal.

In using the device of FIG. 3B to treat an atheromatous lesion in the LAD artery, the device is inserted having constrictor 10 positioned in the left main coronary artery and constrictor 20 positioned in the LCx artery as shown in FIG. 4C. Constrictor 10 is slowly expanded to obstruct the left main coronary artery. The pressure in the left main coronary artery and the pressure in the LCx distal to the constrictor can be measured, respectively, by manometers 15 and 25. Blood flow in LAD artery 101 reverses to pass over the atheromatous lesion and into LCx artery 102. If flow reversal dose not occur due to insufficient blood flow from the collateral circulation to the LAD, i.e., insufficient pressure gradient between the LAD and the LCx, constrictor 20 is expanded to further reduce the LCx pressure to create a favorable pressure gradient between the LAD and the LCx to reverse blood flow into the LCx. Optional filter 55 mounted on wire 50 may be deployed distal constrictor 20 to prevent distal embolization of the LCx artery.

Figure 5A:
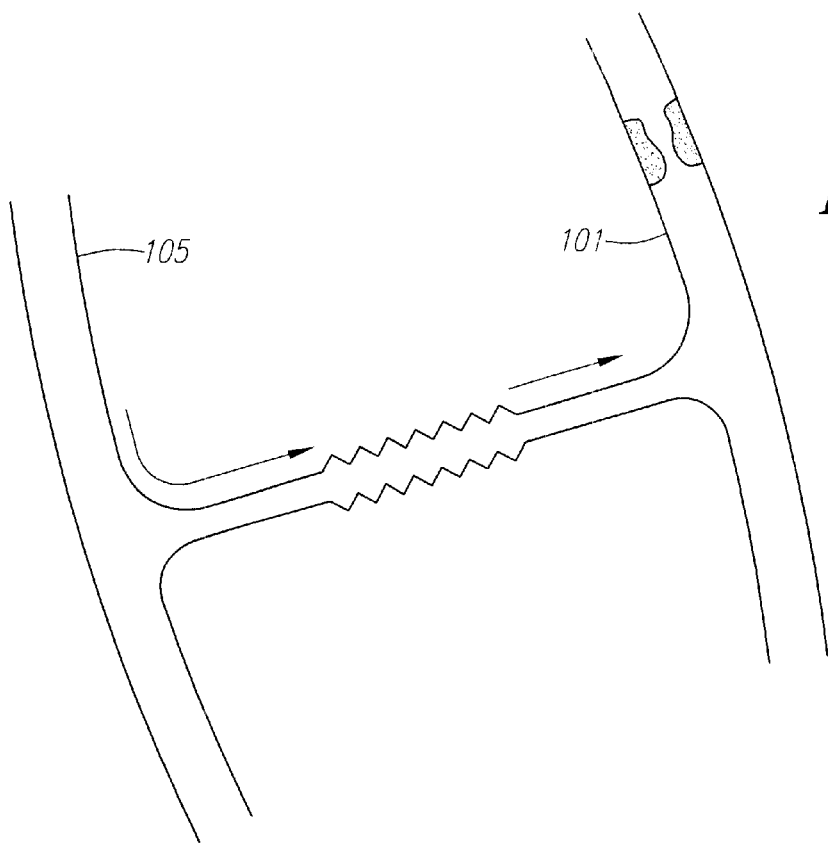
FIG. 5A depicts an occluding lesion in the left circumflex artery.
Figure 5B:
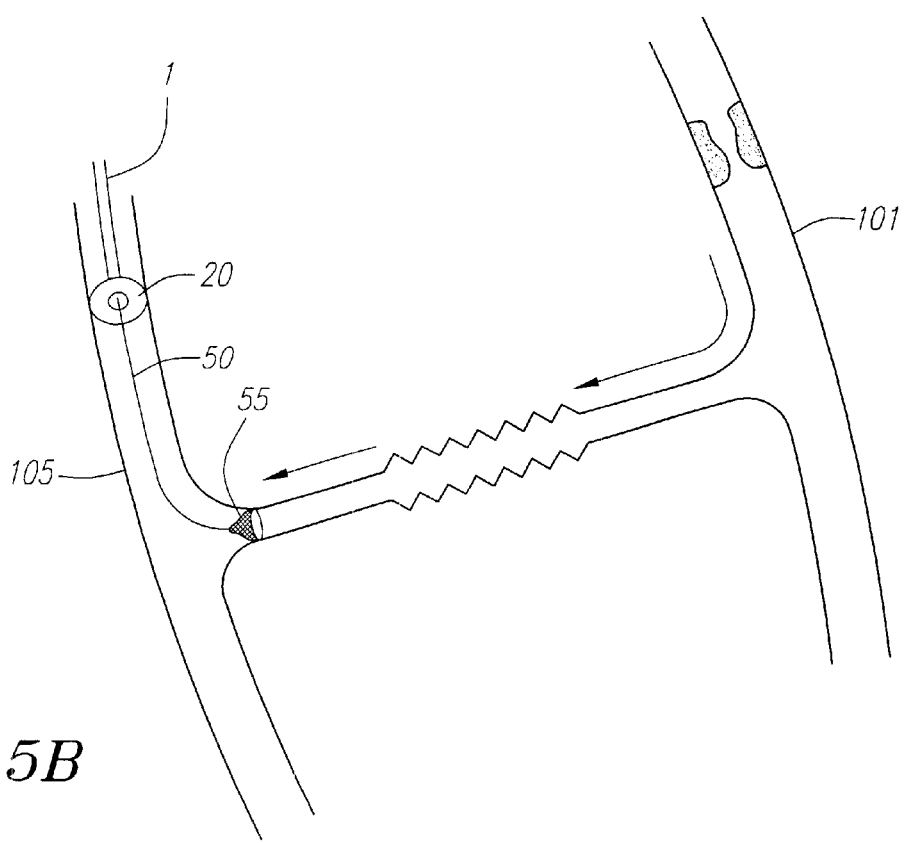
FIG. 5B depicts the use of an occluder to establish flow reversal from the left circumflex artery to the right coronary artery.

FIG. 5A depicts collateral circulation between right coronary artery 105 and LAD artery 101 having an occluding lesion in the LAD. The ischemic myocardium supplied by the LAD distal to the occluding lesion generally receives some blood supply from RCA. To treat the occluding lesion in the LAD using the flow reversal concept and the device of FIG. 1B, the distal end of device 1 having constrictor 20 is inserted and positioned in RCA 105 as shown in FIG. 5B. The constrictor is slowly expanded to constrict RCA 105, causing progressive decline in the distal RCA pressure. At a critically low pressure in the distal RCA, blood flow in distal LAD artery 101 reverses across the collateral circulation into RCA 105. The reversal of blood flow in the LAD and into the RCA can be verified fluoroscopically with dye. After reversal of blood flow is established, a therapeutic instrument, such as an angioplasty catheter, stent deployment catheter, or atherectomy catheter, can be inserted through the lumen of device 1 to treat the atheromatous lesion. Embolic materials generated during the procedure are diverted into the RCA, thereby minimizing distal embolization down the LAD artery. To prevent distal embolization of the RCA, filter 55 mounted on guidewire 50 or a catheter may be inserted through the lumen of device 1 and deployed in the RCA as shown in FIG. 5B.

Figure 6A:
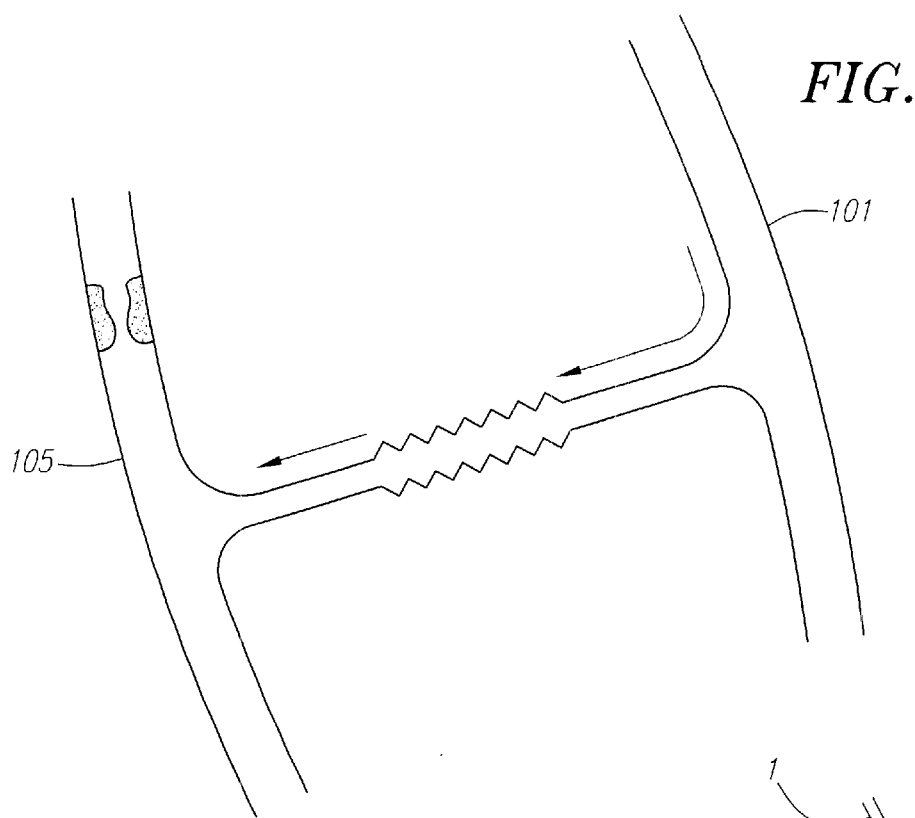
FIG. 6A depicts an occluding lesion in the right coronary artery.
Figure 6B:
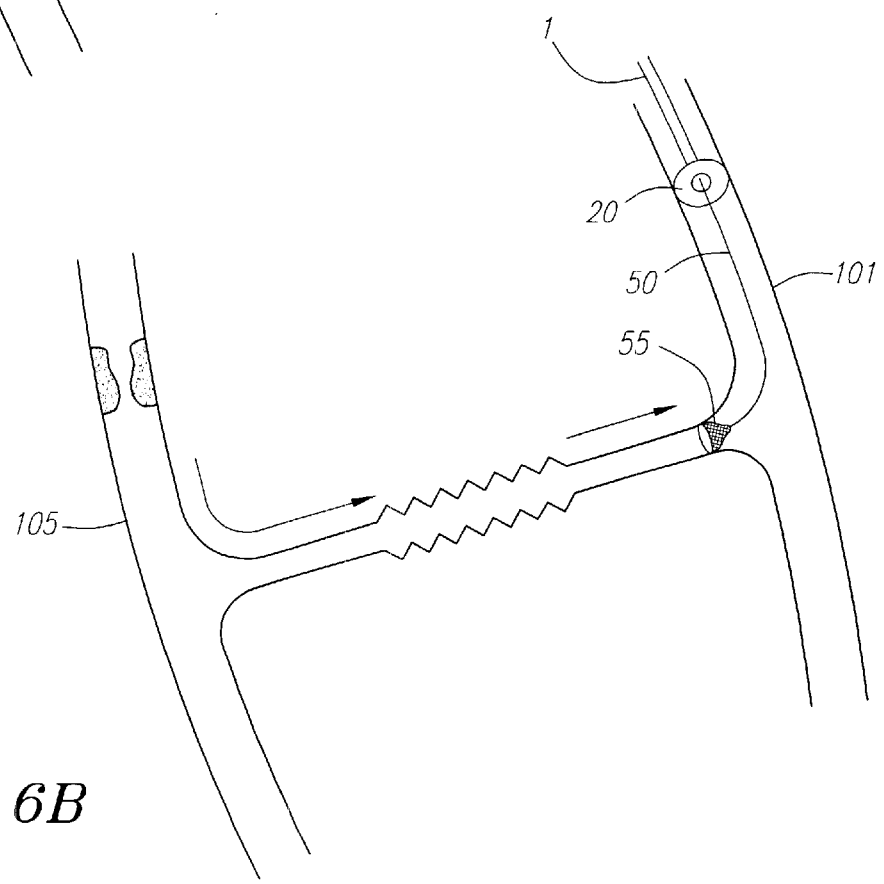
FIG. 6B depicts the use of an occluder to establish flow reversal from the right coronary artery to the left circumflex artery and a filter deployed in a branch of the left circumflex artery to prevent distal embolization.
Figure 6C:
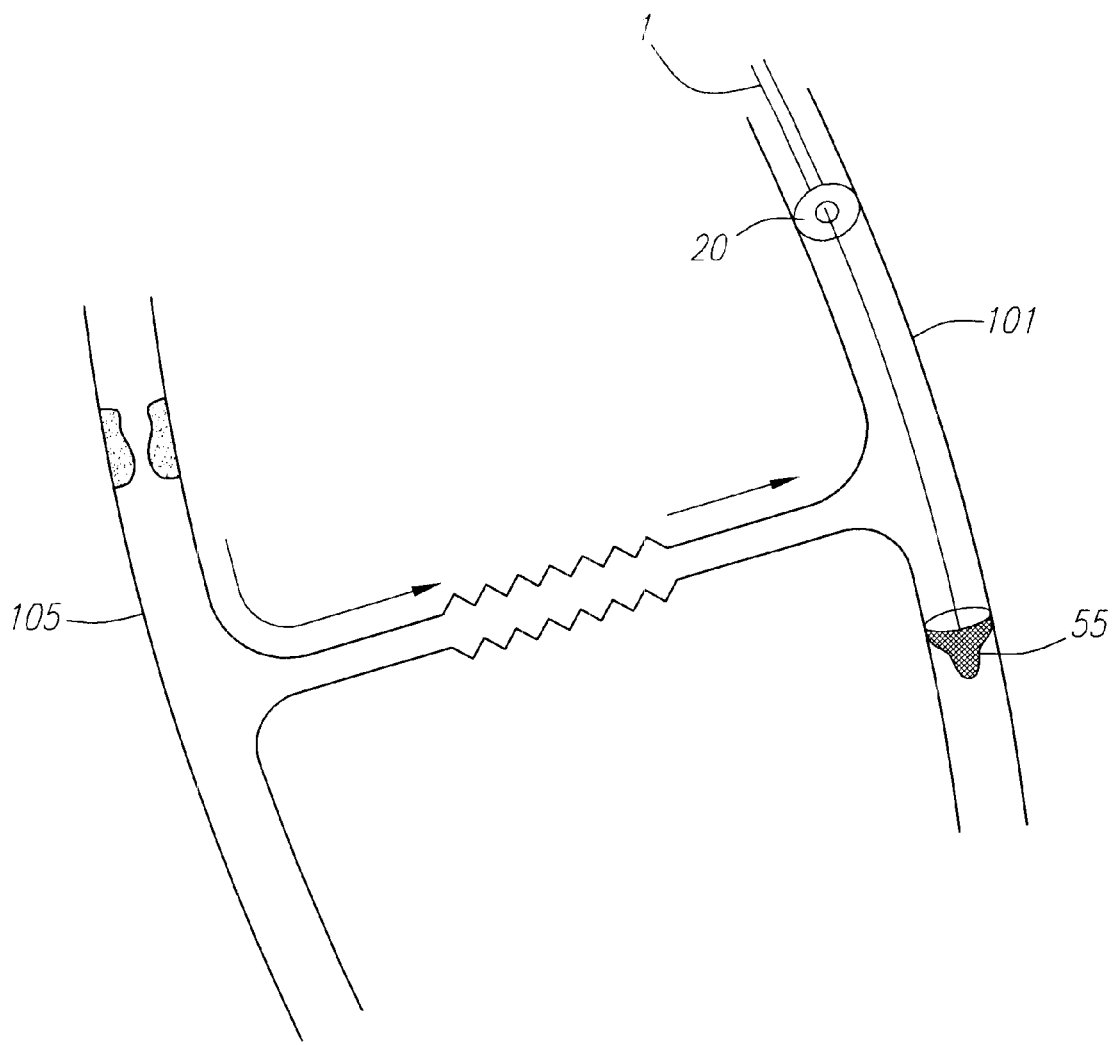
FIG. 6C depicts a filter deployed in the distal left circumflex artery of FIG. 6B to prevent distal embolization.

When an occluding lesion is located in the RCA as depicted in FIG. 6A, the myocardium supplied by the RCA distal the occluding lesion generally receives some blood supply from collateral circulation through the LAD artery. To treat the occluding lesion using the flow reversal concept and device of FIG. 1B, constrictor 20 is inserted and slowly expanded to constrict LAD 101, causing progressive decline in the distal LAD arterial pressure. At a critically low pressure in the distal LAD artery, blood flow in distal RCA 105 reverses across the collateral circulation into LAD artery 101. After reversal of blood flow is confirmed fluoroscopically, a therapeutic instrument, such as an angioplasty catheter, stent deployment catheter, or atherectomy catheter, can be inserted through the lumen of device 1 to treat the atheromatous lesion. Embolic materials generated during the procedure are diverted into the LAD artery, thereby minimizing distal embolization down the RCA artery. To prevent distal embolization to the LAD artery, filter 55 may be inserted through the lumen of device 1 and deployed in a branch of the LAD artery. Alternatively, filter 55 may be deployed in the distal LAD as shown in FIG. 6C.

Figure 7A:
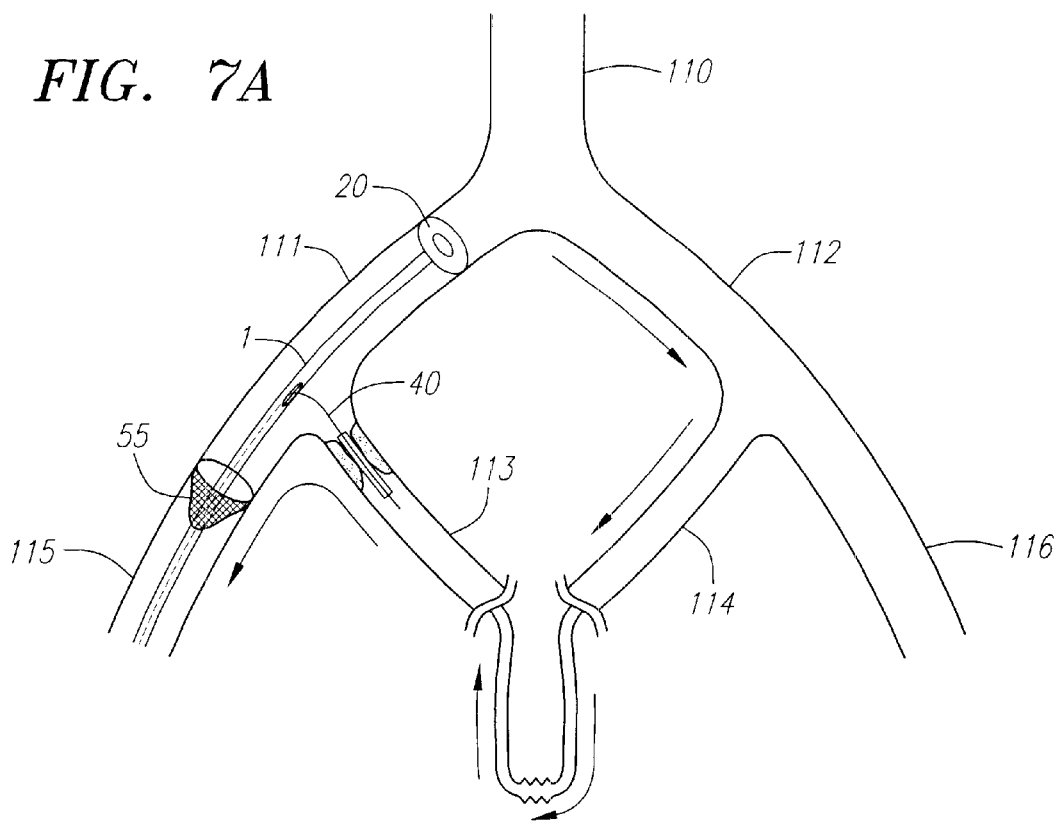
FIG. 7A depicts the device of FIG. 1B inserted through the right femoral artery to establish flow reversal from the right internal iliac artery to the right external iliac artery to treat an occluding lesion in the right internal iliac artery.
Figure 7B:
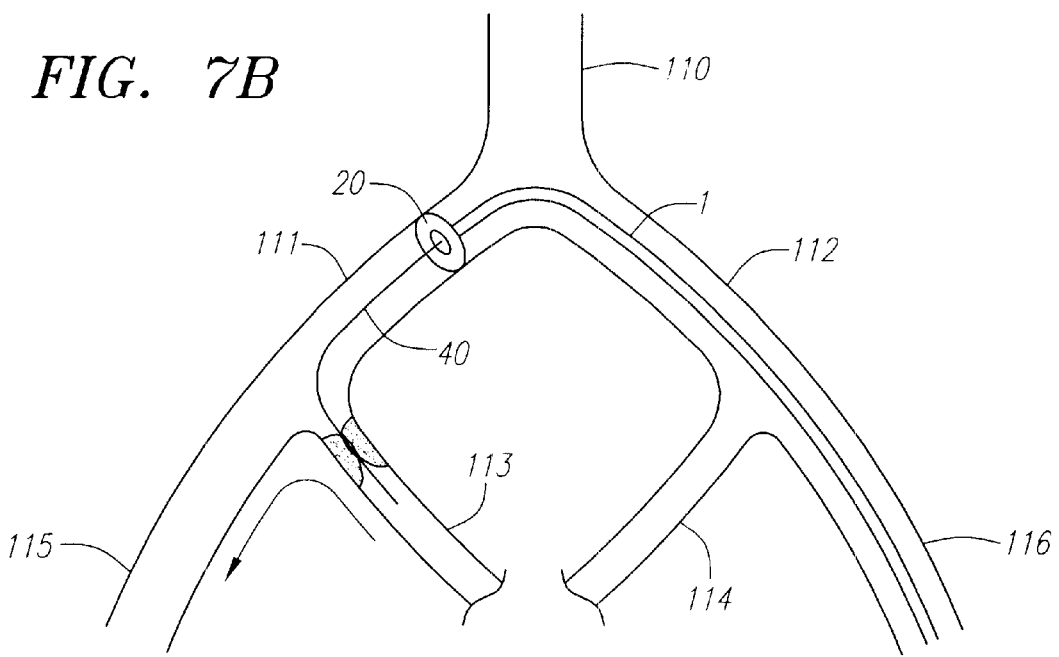
FIG. 7B depicts the device of FIG. 1B inserted through the left femoral artery to establish flow reversal from the right internal iliac artery to the right external iliac artery to treat an occluding lesion in the right internal iliac artery.
Figure 8:
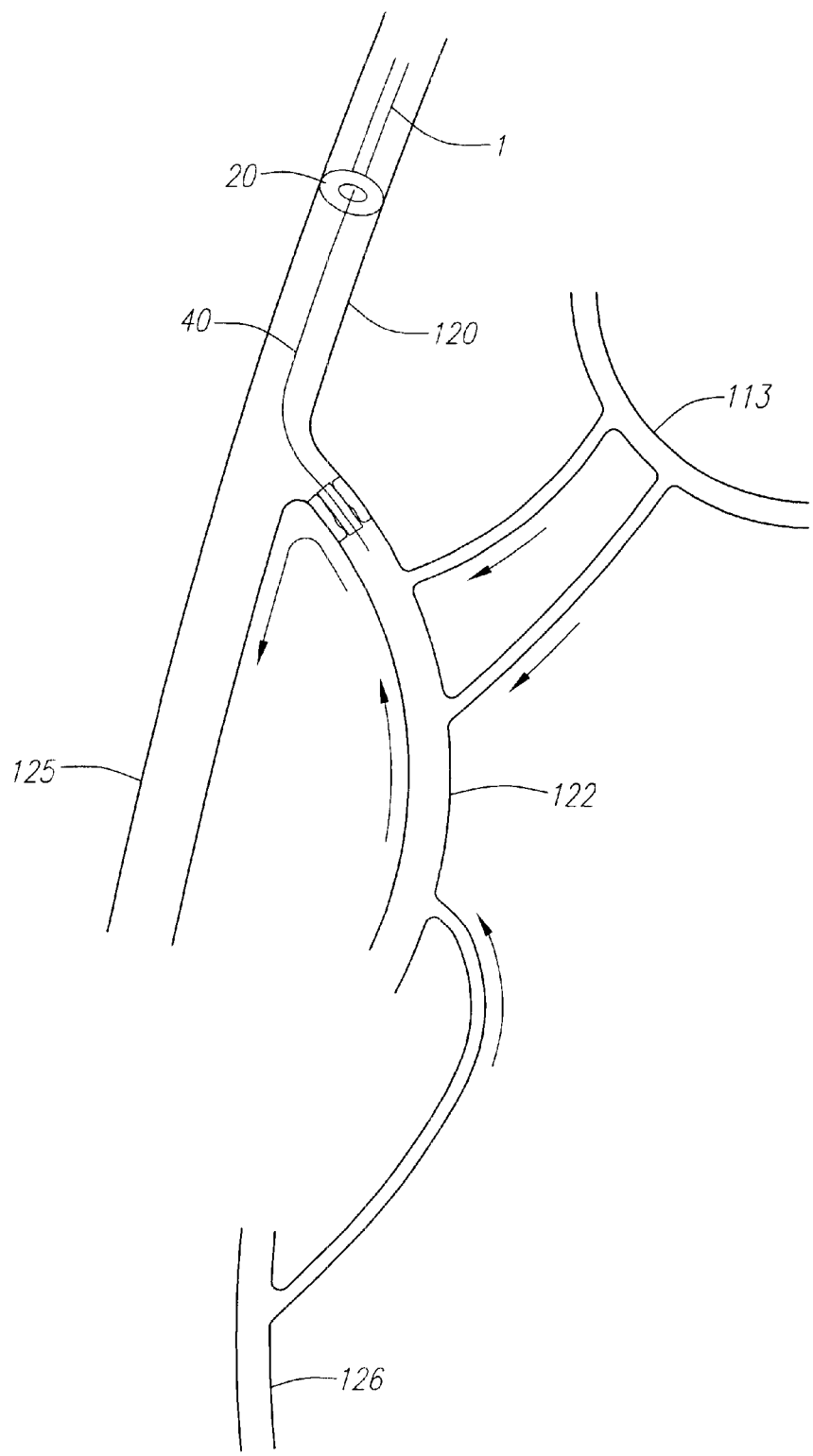
FIG. 8 depicts the device of FIG. 1B inserted in the right common femoral artery to establish flow reversal from the right perfunda femoris artery to the right superficial femoral artery to treat an occluding lesion in the right profunda femoris artery.

FIGS. 7A and 7B illustrate another example of using the devices disclosed herein to establish flow reversal in arteries having collateral circulation. Abdominal aorta 110 bifurcates into (1) right common iliac artery 111, which branches into right external iliac artery 115 and right internal iliac artery 113, and (2) left common iliac artery 112, which branches into left external iliac artery 116 and left internal iliac artery 114. The right and left internal iliac arteries supply the pelvic organs and are well collateralized. When occlusion occurs in right internal iliac artery, as shown in FIG. 7A, flow reverses in the distal right internal iliac artery to supply ischemic organs through collateral vessels branching from the left internal iliac artery and the deep femoral arteries. By having constrictor 20 inserted in right common iliac artery 111, the reversal of blood flow from the right internal iliac artery down the right external iliac artery is enhanced. Catheter 40 carrying a therapeutic instrument, such as an atherectomy device, at its distal end is inserted through the lumen of device 1 to treat the occluding lesion in the right internal iliac artery. Vascular debris generated during the procedure is then diverted away from the right internal iliac artery and down the right external iliac artery. Device 1 may be inserted through the right femoral artery into the right common iliac artery as depicted in FIG. 7A, or through the left femoral artery, crossing the iliac bifurcation, and down the right common iliac artery as shown in FIG. 7B. It will be understood that a blood filter may optionally be included on catheter 1 (FIG. 7A), or may be inserted through the lumen of device 1 or independently in the right external iliac artery or the right femoral artery to prevent distal embolization of vascular debris generated from treating the internal iliac occlusion.

Where the right external iliac artery extends beyond the right inguinal ligament, it becomes right common femoral artery 120 which branches distally into right superficial femoral artery 125 and right profunda femoris artery 122 as depicted in FIG. 8. The profunda femoris artery is well collateralized with internal iliac branches and right popliteal artery 126. When an occlusion occurs in the right profunda femoris artery, which supplies muscles of the right thigh, blood flow in the collateral vessels reverses to supply the ischemic muscle distal the occluding lesion. By positioning an expanded constrictor/occluder in right common femoral artery 120, blood flow up the right profunda femoris artery is enhanced, causing blood flow across the occluding lesion, and down right superficial femoral artery 125. Vascular debris generated during treatment of the occluding lesion by therapeutic catheter 40 is diverted down the superficial femoral artery. A filter may optionally be positioned in right superficial femoral artery 125 to capture debris.

The length of catheter will generally be between 10 and 200 centimeters, preferably approximately between 30 and 150 centimeters. The inner diameter of the catheter lumen will generally be between 0.2 and 0.8 centimeters, preferably approximately between 0.3 and 0.5 centimeters. The diameter of the expanded occluder will generally be between 0.3 and 2 centimeters, preferably approximately 0.5 and 1.0 centimeter. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, the devices and features shown in any depicted embodiment can be used in any other depicted embodiment. Moreover, each of the first constrictor, second constrictor, and filter may or may not be present, whether or not they are depicted in any given embodiment.

What is claimed is:

1. A method for flow reversal in a vessel having a proximal segment that branches into first and second distal segments, the first distal segment having a lesion and a source of collateral flow, the method comprising the steps of:

inserting the distal end of a catheter into the proximal segment, the catheter having a proximal end, a distal end, and an expandable device on a distal region of the catheter;

locating the expandable device within the proximal segment;

expanding the expandable device to at least partially obstruct the proximal segment, wherein flow in the first distal segment is reversed to pass over the lesion and into the second distal segment.

2. The method of claim 1, wherein the proximal segment is a common carotid artery, the first distal segment is an internal carotid artery, and the second distal segment is an external carotid artery.

3. The method of claim 1, wherein the proximal segment is a left main coronary artery, the first distal segment is a left anterior descending coronary artery, and the second distal segment is a left circumflex coronary artery.

4. The method of claim 1, wherein the proximal segment is a common femoral artery, the first distal segment is a profunda femoris, and the second distal segment is a superficial femoral artery.

5. The method of claim 1, wherein the proximal segment is a common iliac artery, the first distal segment is the internal iliac artery, and the second distal segment is an external iliac artery.

6. The method of claim 1, further comprising the steps of inserting a second expandable device in the second distal segment and expanding the second expandable device to at least partially obstruct the second distal segment.

7. The method of claim 1, further comprising the step of inserting a filter in the second distal segment to capture debris in the second distal segment.

8. The method of claim 1, wherein the vessel is an artery.

9. The method of claim 1, wherein the vessel is a vein.

10. The method of claim 1, wherein the vessel is a lymphatic duct.

11. The method of claim 1, further comprising the step of injecting an angiographic dye to confirm flow reversal.

12. The method of claim 1, further comprising the step of treating the lesion with an interventional catheter.

13. The method of claim 12, wherein the catheter is an angioplasty catheter.

14. The method of claim 12, wherein the catheter is an atherectomy catheter.

15. The method of claim 12, wherein the catheter is a stent deployment catheter.

* * * * *